US012778740B2

(12) United States Patent
Kam

(10) Patent No.: US 12,778,740 B2
(45) Date of Patent: Nov. 3, 2026

(54) TWO-WAY ADJUSTABLE LOOP SUSPENSORY DEVICE

(71) Applicant: CONMED CORPORATION, Utica, NY (US)

(72) Inventor: Andrew Kam, Odessa, FL (US)

(73) Assignee: CONMED CORPORATION, Utica, NY (US)

( * ) Notice: Subject to any disclaimer, the term of this patent is extended or adjusted under 35 U.S.C. 154(b) by 1614 days.

(21) Appl. No.: 16/645,760

(22) PCT Filed: Sep. 6, 2018

(86) PCT No.: PCT/US2018/049698

§ 371 (c)(1),
(2) Date: Mar. 9, 2020

(87) PCT Pub. No.: WO2019/051050

PCT Pub. Date: Mar. 14, 2019

(65) Prior Publication Data

US 2020/0281712 A1 Sep. 10, 2020

Related U.S. Application Data

(60) Provisional application No. 62/555,081, filed on Sep. 7, 2017.

(51) Int. Cl.
*A61F 2/08* (2006.01)
*A61B 17/04* (2006.01)

(52) U.S. Cl.
CPC ........ *A61F 2/0811* (2013.01); *A61B 17/0401* (2013.01); *A61B 2017/0459* (2013.01);
(Continued)

(58) Field of Classification Search
CPC ............ A61F 2/0811; A61F 2002/0852; A61F 2002/0882; A61F 2250/0007;
(Continued)

(56) References Cited

U.S. PATENT DOCUMENTS

| | | | |
|---|---|---|---|
| 8,439,976 | B2 | 5/2013 | Albertorio et al. |
| 10,398,426 | B2 | 9/2019 | Burkhart et al. |

(Continued)

FOREIGN PATENT DOCUMENTS

| | | |
|---|---|---|
| EP | 3323386 | 5/2018 |
| FR | 2 980 356 | 3/2013 |

(Continued)

OTHER PUBLICATIONS

International Search Report Form PCT/ISA/220, International Application No. PCT/US2018/049698, pp. 1-17, Dated Jan. 23, 2019.

(Continued)

*Primary Examiner* — Thomas C Barrett
*Assistant Examiner* — Mikail A Mannan
(74) *Attorney, Agent, or Firm* — Bond, Schoeneck & King, PLLC; Frederick J.M. Price

(57) ABSTRACT

Devices for fixation of a soft tissue graft at a surgical site. A suspensory graft fixation device (100) for securing a replacement graft ligament in a bone tunnel includes an elongated anchor member (102) with top (114) and bottom (116) surfaces, and adjacent first (110) and second (112) suture receiving apertures extending from the top surface to the bottom surface thereof. A graft supporting loop element is attached to the anchor member and is formed of a suture (104) having first and second limbs (124, 126). The suture is threaded through the first and second suture receiving apertures such that first and second loops (132, 134) are formed in the suture. The first and second loops extend from the bottom surface, while the first and second limbs extend from the top surface. A splice (136) is formed in the second limb extending from the top surface and the first limb extends through the splice.

7 Claims, 8 Drawing Sheets

(52) U.S. Cl.
CPC ................. *A61F 2002/0852* (2013.01); *A61F 2002/0882* (2013.01); *A61F 2250/0007* (2013.01); *A61F 2310/00023* (2013.01)

(58) Field of Classification Search
CPC .... A61F 2310/00023; A61F 2002/0841; A61F 2002/087; A61F 2002/0888; A61F 2250/0012; A61F 2/0805; A61B 17/0401; A61B 2017/0459; A61B 2017/0406; A61B 2017/06185; A61B 2017/0464; A61B 17/0485; A61B 2017/0404; A61B 17/0487; A61B 2017/0412; A61B 2017/0414; A61B 2017/0458; A61B 2017/0496; A61B 17/0469
See application file for complete search history.

(56) References Cited

U.S. PATENT DOCUMENTS

2011/0087280 A1* 4/2011 Albertorio ............ A61F 2/0811 606/232
2015/0039026 A1* 2/2015 Pasquali .......... A61B 17/06166 606/228
2017/0105716 A1* 4/2017 Burkhart ............ A61B 17/0485

FOREIGN PATENT DOCUMENTS

| | | | |
|---|---|---|---|
| JP | 2014171896 | A | 9/2014 |
| KR | 1020140022905 | | 2/2014 |
| KR | 1020140121842 | | 10/2014 |
| WO | WO2012154922 | A2 | 11/2015 |
| WO | 2017/127277 | | 7/2017 |

OTHER PUBLICATIONS

Japan Office Action, Application 2020-513277, dated Apr. 6, 2021, pp. 1-10.
Korea Office Action, App. No. 10-2020-7006585, dated Jun. 16, 2021, pp. 1-12.
CN Office Action, dated Jul. 7, 2017, App. No 201880068230.8, pp. 1-9.

* cited by examiner

TWO-WAY ADJUSTABLE LOOP SUSPENSORY DEVICE

CROSS-REFERENCE TO RELATED APPLICATIONS

This application claims priority to U.S. Provisional Patent Application Ser. No. 62/555,081, filed on Sep. 7, 2017 and entitled "2-Way Adjustable Loop Suspensory Device."

BACKGROUND OF THE INVENTION

1. Field of the Invention

The present disclosure is directed generally to surgical devices for repair and reconstruction of soft tissue injuries and, more particularly, to devices and methods for fixation of a soft tissue graft at a surgical site.

2. Description of Related Art

Many common surgical procedures involve the repair and reconstruction of torn or damaged soft tissue. For example, in common arthroscopic surgical procedures, a replacement graft ligament is secured at the site of the original, now damaged, ligament. The repair and reconstruction of torn or damaged soft tissues is a common surgical procedure. For example, replacement graft ligaments may be secured at the site of the original ligament. The procedure generally involves drilling bone tunnels into adjacent bones at the site of the original ligament and securing a graft ligament within these bone tunnels. In many applications, such as in the knee joint, such procedures may be performed arthroscopically. The graft ligament may be an autograft, an allograft, a xenograft, or it may be totally artificial and synthetic. Common types of anterior cruciate ligament (ACL) grafts, for example, include ones which may be autologous or allograft bone-patellar tendon-bone or soft tissue (such as semitendinosus and gracilis tendons), both types harvested by techniques well known to those skilled in the art.

The graft ligaments may be secured within the bone tunnels in a variety of ways. Of prime importance is the degree to which they can withstand pullout forces prior to complete healing. For example, it is known to use interference screws inserted parallel to the tunnel axis to compress the ends of the graft ligament against the wall of the bone tunnel to secure the graft ligament and promote tissue in-growth.

Suspensory graft fixation devices have been developed to secure a graft ligament in a bone tunnel. One such device is described in U.S. Pat. No. 8,852,250 (Lombardo et al.), entitled Graft Fixation Implant, assigned to the assignee hereof and incorporated by reference herein. Suspensory graft fixation devices work by lying transversely across the opening of a bone tunnel and generally take the form of an elongated anchor member which suspends a graft retaining loop from a fixation point on the surface of a bone to which the graft is to be attached (in this case, a femur). The elongated member has an axis and a pair of suture receiving apertures symmetrically situated on the axis on opposite sides of the center of the elongated member. In ACL procedures the elongated member, often called a button, is adapted to be situated transversely across the exit opening of the bone tunnel on the lateral femoral cortex so that a supporting loop, generally made of suture material, can be suspended from the button and can extend into the bone tunnel from the suture receiving apertures of the button. The suture loop supports one end of a graft ligament passed through the loop.

The term "suture" as used herein may be any type of filamentous material such as a biocompatible or bioabsorbable filament, ribbon, tape, woven or non-woven material capable of providing the loop support and the frictional resistance required by the device described herein. In arthroscopic procedures, such as an ACL reconstruction, the elongated anchor member is initially aligned with the axis of the bone tunnel, and pulled through the tunnel to the exit at the distal end on the lateral femur. For such suspensory graft fixation devices to be able to support a graft ligament and to be properly transversely situated at the exit of the bone tunnel, the suture loop and the bone tunnel must both be long enough to enable the elongated member to "flip" from an axially aligned orientation to a transverse orientation when it exits the bone tunnel.

Since the supporting loop of such a suspensory device is most often of a fixed length, graft fixation requires preparation of a graft ligament of predetermined length. Furthermore, because conventional art suspensory graft fixation devices have fixed loop lengths they are produced in multiple sizes (ranging, for example, from loop lengths of 15 mm to 60 mm in 5 mm increments in the case of XO Button® implants made by ConMed Corporation, Largo, Fla.) in order to accommodate various graft and tunnel lengths that may be encountered during a surgical procedure. The fixed graft length and variations in tunnel and loop lengths can make conventional suspensory ligament fixation challenging.

Recently, suspensory devices have been made with adjustable loop lengths. See, for example, U.S. patent application 2010/0256677, (Albertorio et al.) published Oct. 7, 2010 and entitled Integrated Adjustable Button-Suture-Graft Construct with Two Fixation Devices. It has been found that the adjustability of the loop length of a suspensory graft fixation device may be achieved in a manner considerably less complex than that described in the aforementioned publication.

At times surgeons may encounter situations where they cannot produce a bone tunnel of adequate length to receive a ligament graft suitable for suspensory fixation. A predetermined length of graft ligament is required to engage a predetermined portion of the bone tunnel for proper healing. For example, a so-called short tunnel ACL reconstruction may present a relatively small (narrow) femur which does not enable formation of an adequately long bone tunnel which means, in turn, the suspensory anchor member cannot be advanced far enough out of the tunnel to flip yet keep enough contact between the graft and the bone tunnel wall. Use of an adjustable loop in such situations could nevertheless enable the surgeon to proceed with a suspensory-type repair.

In instances in which soft tissue is to be pulled into a bone tunnel, such as ACL reconstruction, it is desired to have an adjustable loop to simplify the procedure and maximize the bone to soft tissue interface.

Description of the Related Art Section Disclaimer: To the extent that specific patents/publications/applications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/applications/products are discussed above in this Description of the Related Art Section and/or throughout the application, the descriptions/disclosures of which are all hereby incorporated by reference into this document in their respective entirety(ies).

SUMMARY OF THE INVENTION

Embodiments of the present invention recognize that there are potential problems and/or disadvantages with conventional suspensory graft fixation devices (as discussed herein and above). Various embodiments of the present invention may be advantageous in that they may solve or reduce one or more of the potential problems and/or disadvantages discussed herein.

The present disclosure is directed to devices and methods for fixation of a soft tissue graft at a surgical site. It is an object of this invention to produce a suspensory graft ligament repair system suitable for short tunnel repairs.

It is another object of this invention to produce a suspensory graft fixation device adapted to lock the size and position of the graft supporting loop after it has been set at a desired length.

It is also an object of this invention to automatically lock the graft supporting loop by pulling it in one direction relative to the anchor member, and to vary the length of the graft supporting loop, to resize it, by pulling it in the opposite direction.

It is yet another object of this invention to correct for instances of over-tensioning of the graft or if the graft has been advanced too far into the bone tunnel.

In one aspect, a suspensory graft fixation device for securing a replacement graft ligament in a bone tunnel is provided. The suspensory graft fixation device includes an elongated anchor member with top and bottom surfaces, and adjacent first and second suture receiving apertures extending from the top surface to the bottom surface thereof. A graft supporting loop element is attached to the anchor member and is formed of a suture having first and second limbs. The suture is threaded through the first and second suture receiving apertures such that first and second loops are formed in the suture. The first and second loops extend from the bottom surface, while the first and second limbs extend from the top surface. A splice is formed in the second limb extending from the top surface and the first limb extends through the splice.

According to another aspect, the suspensory graft fixation device includes an elongated anchor member having a top surface and a bottom surface extending between a first end and a second end. A plurality of apertures extend from the top surface to the bottom surface of the elongated anchor member. At least two of the plurality of apertures are adjacent first and second suture receiving apertures. The device also includes a graft supporting loop element attached to the anchor member. The graft supporting loop element is formed of a suture having a first limb and a second limb. The suture is threaded through the first and second suture receiving apertures such that first and second loops are formed in the suture and extend from the bottom surface of the elongated anchor member, while the first and second limbs extend from the top surface. A splice is formed in the second limb of suture extending from the top surface of the elongated anchor member and the first limb extends through the splice. Tensioning the first loop pulls the first limb through the splice, lengthening the first loop, and tensioning the second loop pulls the splice over the first suture receiving aperture.

In yet another aspect, a method of suspensory fixation of a replacement graft ligament in a bone tunnel is provided. The method includes the steps of: (i) providing an elongated anchor member having a top surface and a bottom surface, and adjacent first and second suture receiving apertures extending from the top surface to the bottom surface thereof; (ii) providing a suture having a first limb and a second limb with a central biting portion therebetween; (iii) passing the first limb through the first suture receiving aperture from the top surface to the bottom surface and thereafter, passing the first limb through the second suture receiving aperture from the bottom surface to the top surface, creating a first loop in the first limb; (iv) passing the second limb through the second suture receiving aperture from the top surface to the bottom surface and thereafter, passing the second limb through the first suture receiving aperture from the bottom surface to the top surface, creating a second loop in the second limb; (v) creating a splice in the second limb extending from the top surface from the first suture receiving aperture; and (vi) passing the first limb through the splice in the second limb.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
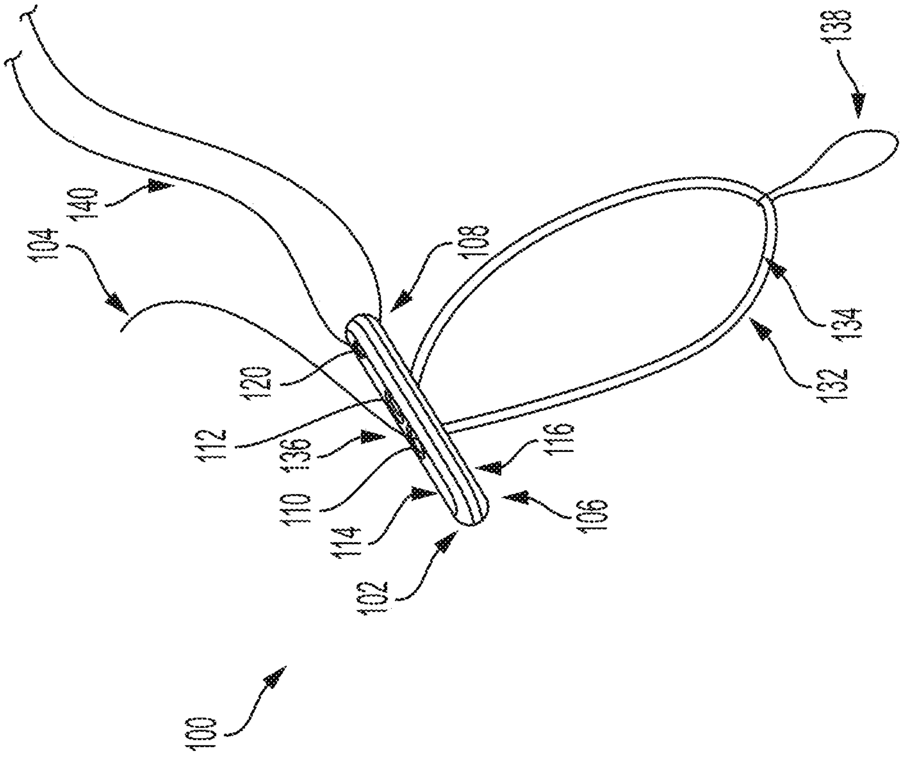
FIG. 1 is a perspective view schematic representation of a suspensory fixation device, according to an embodiment.

Referring now to the figures, wherein like reference numerals refer to like parts throughout, FIG. 1 shows a side perspective view schematic representation of a suspensory graft fixation device 100, according to an embodiment. The device 100 comprises an elongated anchor member 102 and a length of suture 104. In the depicted embodiment, the suture 104 is in the form of a filamentous strand composed of high strength, filamentous material such as ultra-high molecular weight polyethylene. The anchor member 102 can be composed of metal, such as implantable grade titanium, or any other suitable bioabsorbable or biocompatible material (as should be understood by a person of ordinary skill in the art in conjunction with a review of this disclosure). In embodiments, the length of anchor member 102 may range from 12 mm to 20 mm.

Figure 2:
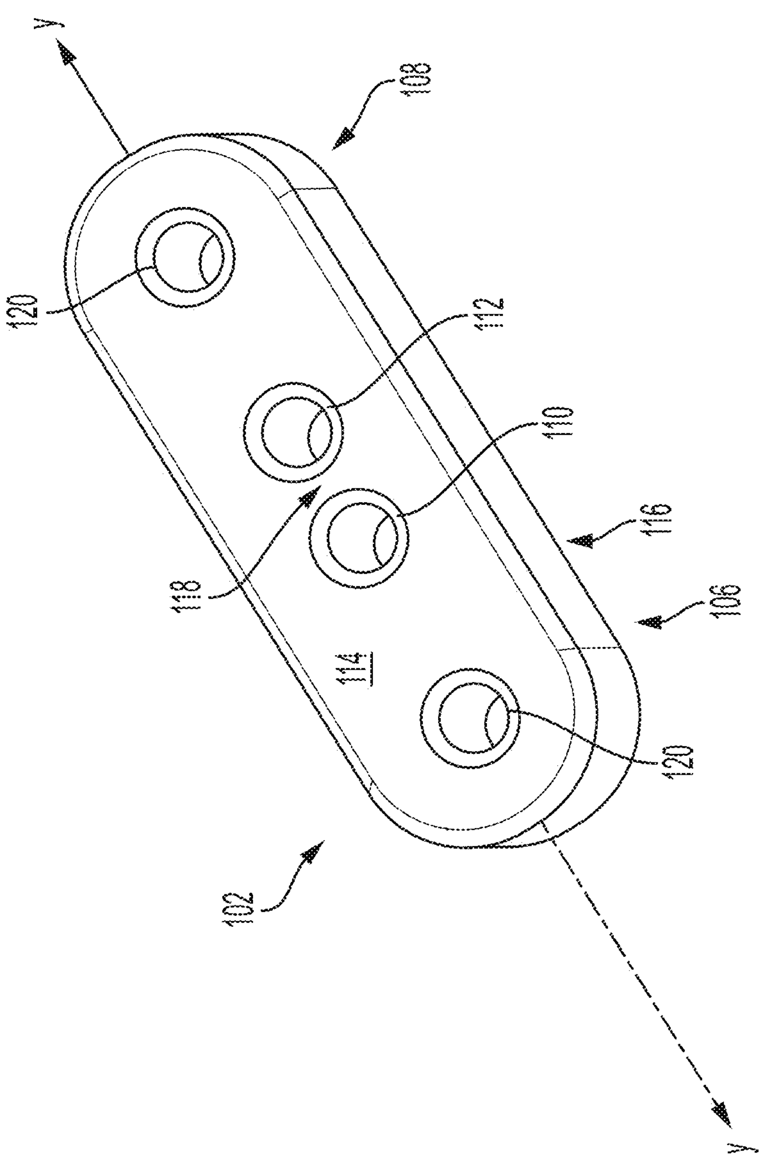
FIG. 2 is a top perspective view schematic representation of the anchor member of the suspensory fixation device, according to an embodiment.
Figure 5:
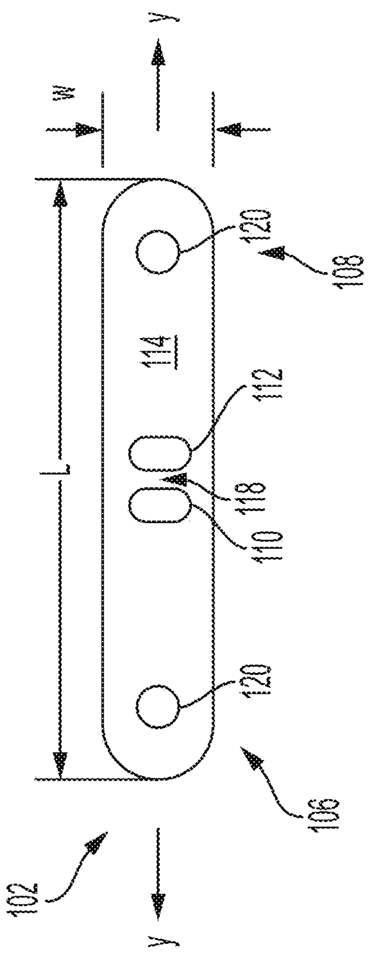
FIG. 5 is a top view schematic representation of a suspensory fixation device, according to an embodiment.

Turning briefly to FIG. 2, there is a top perspective view schematic representation of the anchor member 102 of the suspensory fixation device 100, according to an embodiment. The anchor member 102 extends along a central longitudinal y-y axis between its first end 106 and second end 108. The anchor member 102 also has a pair of central suture receiving apertures 110, 112, which are sized or otherwise configured to receive suture 104 that will form loops. For example, the diameters of suture receiving apertures 110, 112 may be on the order of 1 mm, while the diameter of the suture 104 may be on the order of 1 mm or USP size #5. In an embodiment according to FIG. 5, the anchor member 102 is oblong in geometry. In particular, as shown, a length L of the anchor member 102 is greater than a width w of the anchor member 102. The oblong geometry of the anchor member 102 allows the anchor member 102 to pass through narrow bone tunnels.

Figure 3:
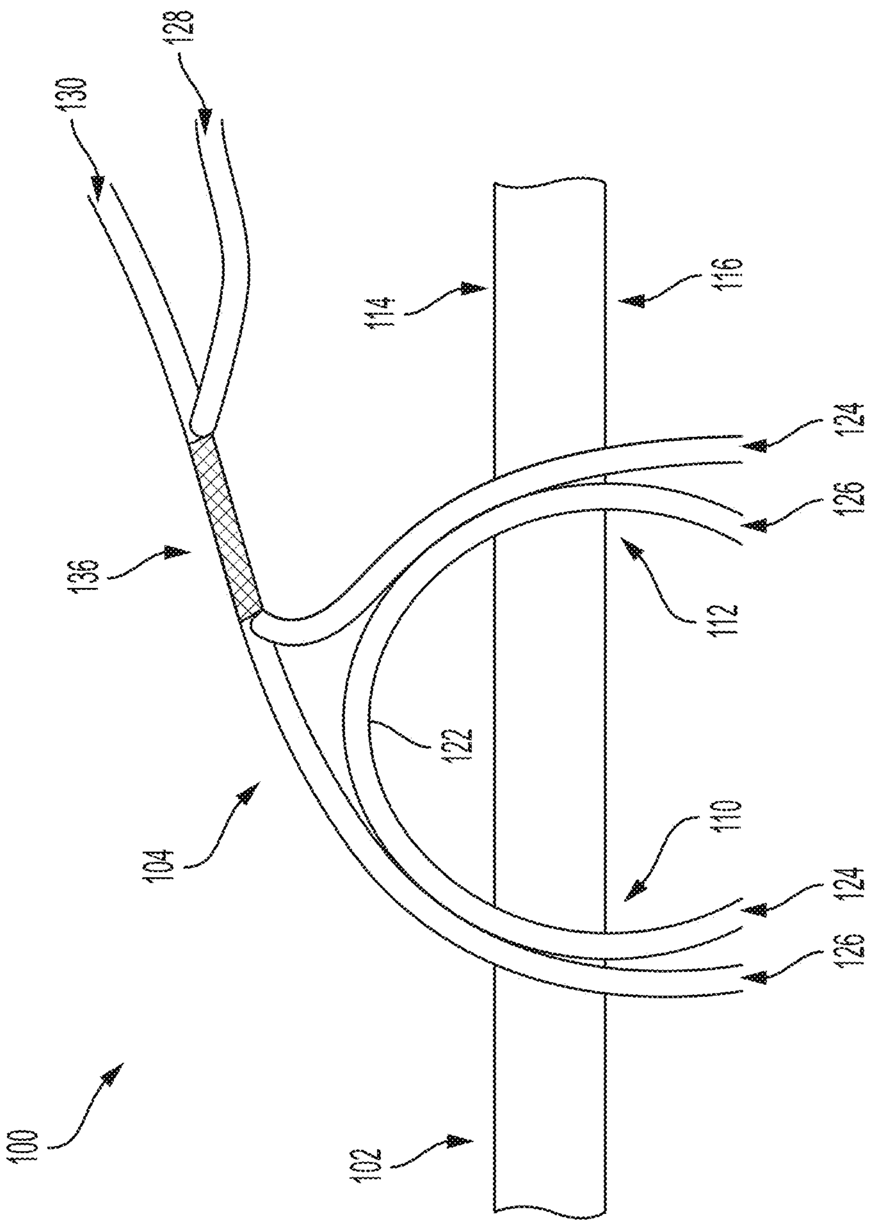
FIG. 3 is a cross-sectional side view schematic representation of the suspensory fixation device, according to an embodiment.
Figure 4:
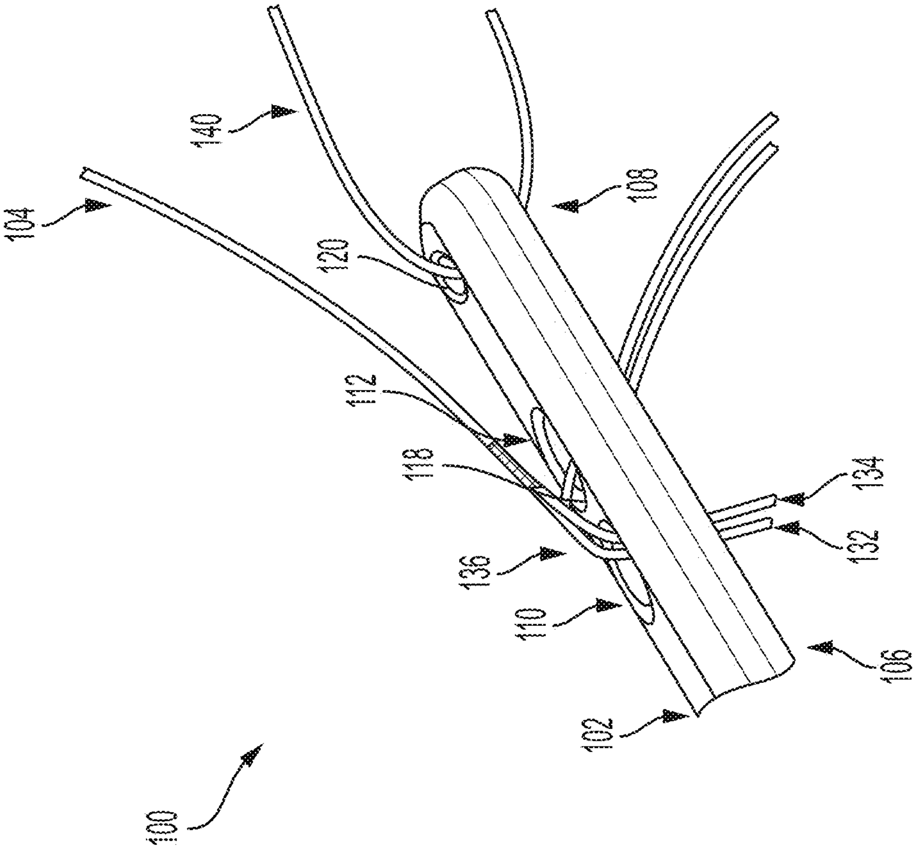
FIG. 4 is a close-up perspective view schematic representation of a suspensory fixation device, according to an embodiment.

Referring back to FIG. 2, the anchor member 102 has a top surface 114 and a bottom surface 116 (best seen in FIGS. 3-4). The bottom surface 116 is sometimes referred to as the proximal surface and is intended to be placed adjacent a bone tunnel exit. As used herein, the term "proximal" refers to the side of the bone containing the bone tunnel (i.e., extending inwardly away from the surface of the lateral femur in an ACL procedure), and the term "distal" refers to the side of the bone against which the transverse anchor member 102 rests (i.e., extending outwardly away from the surface on the lateral femur).

Still referring to FIG. 2, the suture receiving apertures 110, 112 are situated on opposite sides of a central bridge portion 118 extending between them. The anchor member 102 may also optionally have one or more placement apertures 120 extending between the top and bottom surfaces 114, 116. In the depicted embodiment, there is a placement aperture 120 at the first end 106 of the anchor member 102 and a placement aperture 120 at the second end 108 of the anchor member 102. The placement apertures 120 are sized or otherwise configured to receive a placement suture 140 (or another filamentous strand) to facilitate placement of the device 100 at a bone tunnel exit. For example, a placement suture 140 is attached to a placement aperture 120 and pulled through the bone tunnel, facilitating orienting the elongated anchor member 102 parallel to the bone tunnel axis.

As shown in FIG. 1, the suspensory fixation device 100 is designed to have the anchor member 102 operate with a filamentous strand 104 suitable for following a tortuous path through the suture receiving apertures 110, 112 of anchor member 102. In an embodiment, the filamentous strand 104 is a single length of appropriately sized suture. The term "suture" as used herein may be used interchangeably with "filamentous material" and, as described above, will be understood to mean any biocompatible or bioabsorbable strand of material which can, when combined with anchor member 102, operate to support a replacement graft in the manner described below. As will be understood below, the combination of filamentous strand 104 with the features of anchor member 102 can perform different functions along the path of the suture 104 through the suture receiving apertures 110, 112 of the anchor member 102.

Referring now to FIG. 3, there is a cross-sectional side view schematic representation of the suspensory fixation device 100, according to an embodiment. To load the anchor member 102 shown in FIG. 2, the filamentous strand 104 is passed or wrapped through the suture receiving apertures 110, 112. Specifically, as shown in FIG. 3, the filamentous strand 104 is first folded on itself to form a central bight portion 122, thus creating two limbs 124, 126 extending from the central bight portion 122. Each limb 124, 126 has a length extending from the central bight portion 122 to the free, unattached ends 128, 130 of the limbs 124, 126.

Still referring to FIG. 3, the first limb 124 is passed through a first suture receiving aperture 110 and the second limb 126 is passed through a second suture receiving aperture 112 (in the downward direction as shown in FIG. 3). The first and second limbs 124, 126 extend through the suture receiving apertures 110, 112 from the top surface 114 of the anchor member 102 to the bottom surface 116 of the anchor member 102. The second limb 126 is then passed up through the first suture receiving aperture 110 from the bottom surface 116 of the anchor member 102 to the top surface 114 of the anchor member 102. Similarly, the first limb 124 is passed up through the second suture receiving aperture 112 from the bottom surface 116 of the anchor member 102 to the top surface 114 of the anchor member 102. As shown in FIG. 3, the central bight portion 122 extends over the central bridge portion 118 on the top surface 114 of the anchor member 102, while two adjustable loops 132, 134 extend from the suture receiving apertures 110, 112 through the bottom surface 116 of the anchor member 102, as shown in FIG. 1.

With the free, unattached ends 128, 130 extending from the top surface 114 of the anchor member 102, a splice 136 is created in the second limb 126, as shown in FIG. 3. The first limb 124 is passed through the splice 136, forming a jacket around the first limb 124. In the depicted embodiment, the splice 136 is adjacent and above (distal to) the central bight portion 122. With the filamentous strand 104 wrapped through the suture receiving apertures 110, 112, creating adjustable loops 132, 134 extending from the bottom surface 116 of the anchor member 102, and the splice 136 extending from the top surface 114 of the anchor member 102, the device 100 can be used to adjustably apply and release tension on a graft at a bone tunnel exit.

While the suture path of an embodiment of device 100 is as shown in FIG. 3, alternate embodiments are feasible. Thus, while the suture path through the anchor member 102 results in device 100 comprising a graft supporting element in the form of two adjustable loops 132, 134, there can be different loop constructions than that described above. For example, the adjustable loops 132, 134 are formed from a single length of suture 104 (or other filamentous material) but in an alternate embodiment, the adjustable loops 132, 134 could be formed by a plurality of individual lengths of suture 104 which together form the adjustable loops 132, 134.

Figure 6:
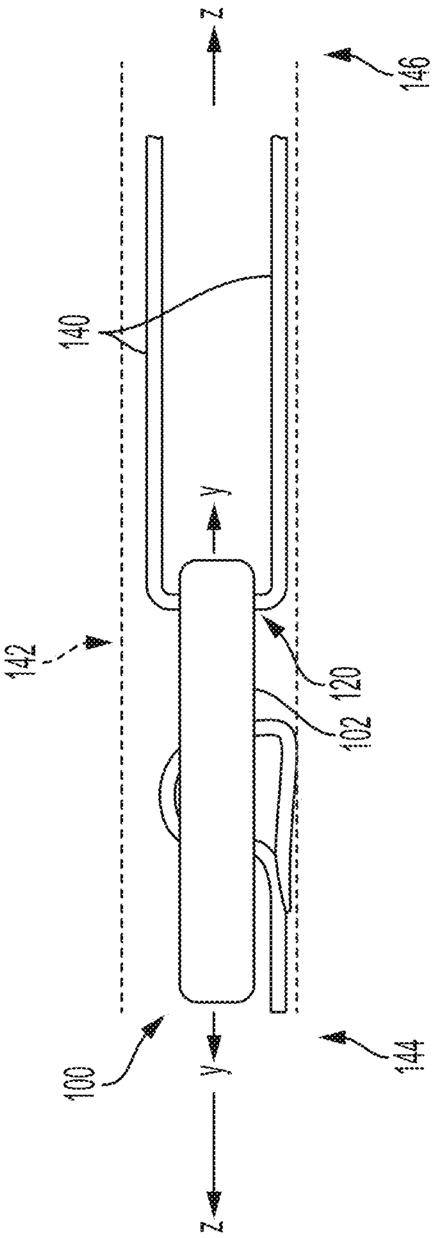
FIG. 6 is a side view schematic representation of a suspensory fixation device in a bone tunnel, according to an embodiment.
Figure 7:
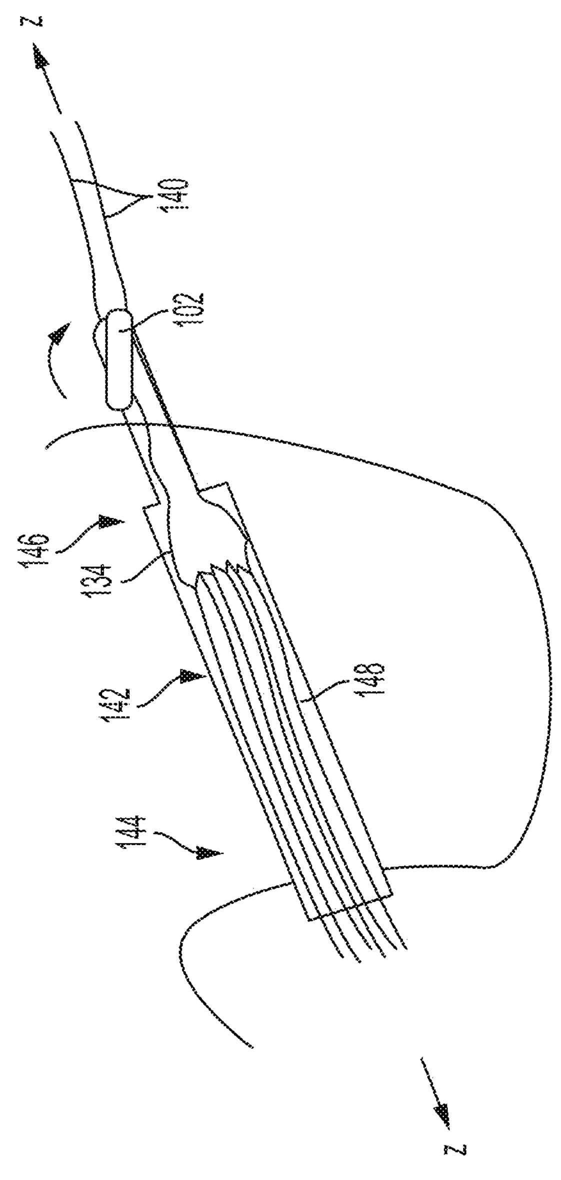
FIG. 7 is a side view schematic representation of a suspensory fixation device in a first configuration attached to a graft and extending from a distal end of a bone tunnel, according to an embodiment.
Figure 8:
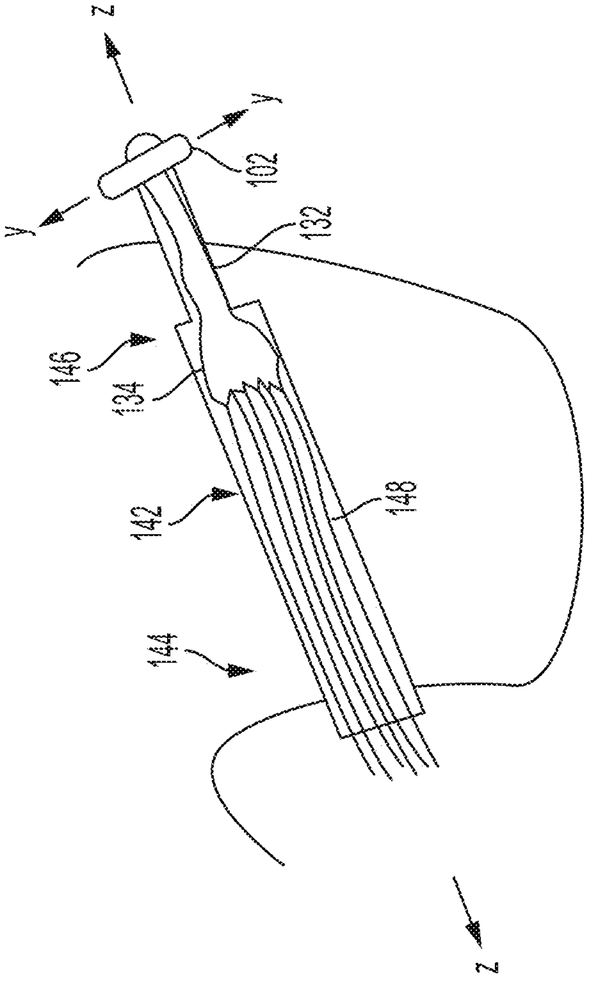
FIG. 8 is a side view schematic representation of a suspensory fixation device in a second configuration attached to a graft and extending from a distal end of a bone tunnel, according to an embodiment.

Turning now to FIGS. 6-8, there are shown side views schematic representations of the device 100 at various configurations during deployment. First, the device 100 shown in FIG. 1 is attached to a graft 148 (FIGS. 7-8). In an embodiment, the graft 148 (FIGS. 7-8) is attached to the second loop 134 and a placement suture 140 is threaded through a placement aperture 120 of the anchor member 102. The placement suture 140 is inserted through the proximal end 144 of the bone tunnel 142 and pulled toward the distal end 146 of the bone tunnel 142. FIG. 6 shows a side view schematic representation of the device 100 in a bone tunnel 142, according to an embodiment. As shown, the placement suture 140 is pulled or otherwise tensioned toward the distal end 146 of the bone tunnel 142. In the depicted embodiment, the placement suture 140 is pulled through the bone tunnel 142, facilitating orienting the elongated anchor member 102 substantially parallel to the bone tunnel axis z-z.

Referring now to FIG. 7, there is shown a side view schematic representation of the device 100 in a first configuration attached to a graft 148 and extending from the distal end 146 of the bone tunnel 142. As shown in FIG. 7, the placement suture 140 is pulled until the anchor member 102 exits the distal end 146 of the bone tunnel 142 and the graft 148 remains within the bone tunnel 142. When using the device 100 to secure the graft 148, the two adjustable loops 132, 134 (also shown in FIG. 1) serve different purposes. The first loop 132, which is created from the first limb 124, functions to resize the lengths of both adjustable loops 132, 134. The second loop 134, which is created from the second limb 126 and attached to the graft 148, functions to lock the device 100 in place, thereby locking the graft 148 in position with respect to the bone tunnel exit (i.e., distal end 146 of the bone tunnel 142).

In use, tension is first applied to the first loop 132, which causes an increase in size of both adjustable loops 132, 134. In one embodiment, a tether 138 (e.g., rope, suture, or other filamentous strand) is attached to the first loop 132, as shown in FIG. 1. When the tether 138 is pulled proximally or otherwise away from the splice 136, slack is introduced into the adjustable loops 132, 134, enlarging the adjustable loops 132, 134. In some cases, the splice 136 is pulled toward the second suture receiving aperture 112 when the first loop 132 is tensioned. However, the splice 136 is too large relative to the second suture receiving aperture 112 and can thus not be pulled through the second suture receiving aperture 112 to the bottom surface 116 of the anchor member 102. Accordingly, additional tension on the first loop 132, pulls the first limb 124 (and the splice 136) proximally to the second suture receiving aperture 112 where the first limb 124 is, due to its size relative to the second suture receiving aperture 112, pulled through the splice 136 and the second suture receiving aperture 112 to provide the extra slack in the adjustable loops 132, 134. At the same time, tension on both adjustable loops 132, 134, by the graft 148, causes the anchor member 102 to rotate. As shown in FIGS. 7-8, the graft 148 (or filament (not shown) attached to the graft 148) can be tensioned or otherwise pulled proximally from the proximal end 144 of the bone tunnel 142, which tensions the adjustable loops 132, 134. The tension from the graft 148 the anchor member 102 to rotate from a first configuration substantially parallel to the bone tunnel axis z-z (FIG. 7) to a second configuration substantially perpendicular to the bone tunnel axis z-z (FIG. 8). When the anchor member 102 is perpendicular across the bone tunnel 142, the anchor member 102 is locked in place by bringing the splice 136 against the first suture receiving aperture 110. Again, the splice 136 is too large relative to the first suture receiving aperture 110 and can thus not be pulled through the first suture receiving aperture 110 to the bottom surface 116 of the anchor member 102. As the splice 136 is created in the second limb 126, the second limb 126 cannot be pulled through the first suture receiving aperture 110 to supply slack and instead locks the device 100.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A suspensory graft fixation device for securing a replacement graft ligament in a bone tunnel, comprising:

an elongated anchor member comprising a top surface and a bottom surface, and adjacent first and second suture receiving apertures extending from the top surface to the bottom surface thereof;

a graft supporting loop element attached to the anchor member, the graft supporting loop element formed of a suture comprising a first limb and a second limb having a first free end and a second free end, respectively;

wherein the suture is threaded through the first and second suture receiving apertures such that first and second loops are formed in the suture and extend from the bottom surface of the elongated anchor member, while the first free end of the first limb extends from the bottom surface through the first receiving aperture to and away from the top surface and the second free end of the second limb extends from the bottom surface through the second receiving aperture to and away from the top surface, and a splice is formed in the second limb of suture extending from the top surface of the elongated anchor member, and wherein the first limb extends through the splice and the first free end and the second free end directly extend away from the splice.

2. The suspensory graft fixation device of claim 1, further comprising a central biting portion extending between the first limb and the second limb, the central biting portion extending over a central bridge portion of the elongated anchor member between the first and second suture receiving apertures.

3. The suspensory graft fixation device of claim 1, wherein first limb extends from the top surface to the bottom surface through the first suture receiving aperture and from the bottom surface to the top surface through the second suture receiving aperture.

4. The suspensory graft fixation device of claim 1, wherein second limb extends from the top surface to the bottom surface through the second suture receiving aperture and from the bottom surface to the top surface through the first suture receiving aperture.

5. The suspensory graft fixation device of claim 1, wherein the first loop is formed by the first limb.

6. The suspensory graft fixation device of claim 1, wherein the second loop is formed by the second limb.

7. The suspensory graft fixation device of claim 1, wherein the elongated anchor member is composed of titanium.

* * * * *